United States Patent [19]  [11] 4,035,445
Baumgartner  [45] July 12, 1977

[54] HYDROTREATING OF RECYCLED BLOCK COPOLYMER SOLVENT

[75] Inventor: Herman J. Baumgartner, Cypress, Calif.

[73] Assignee: Shell Oil Company, Houston, Tex.

[21] Appl. No.: 642,031

[22] Filed: Dec. 18, 1975

Related U.S. Application Data

[63] Continuation of Ser. No. 497,010, Aug. 8, 1974, abandoned.

[51] Int. Cl.$^2$ .......................................... C08F 6/10
[52] U.S. Cl. ............................................ 260/880 B
[58] Field of Search .......... 208/143, 144, 145, 255, 208/257; 260/880 B

[56] References Cited

U.S. PATENT DOCUMENTS

| | | | |
|---|---|---|---|
| 3,153,027 | 10/1964 | Hagemeyer | 260/94.9 F |
| 3,203,891 | 8/1965 | Holden | 208/255 |
| 3,465,065 | 9/1969 | Moss | 260/880 B |
| 3,823,085 | 7/1974 | Kochie | 208/255 |
| 3,853,748 | 12/1974 | Tabler | 208/255 |
| 3,859,370 | 1/1975 | Carter | 208/143 |
| 3,900,526 | 8/1975 | Johnson | 208/255 |
| 3,959,412 | 5/1976 | Oberlin | 260/880 B |

*Primary Examiner*—Paul R. Michl
*Attorney, Agent, or Firm*—Dean F. Vance

[57] ABSTRACT

A process for the removal of impurities from solvents utilized in a cyclic process for the production of block copolymers is provided which comprises separation of block copolymers from their polymerization solvent, the separated solvent having a stated temperature, and hydrotreatment of the solvent with a heterogeneous hydrogenation catalyst at a weight hour space velocity greater than about two, whereby the undesirable contaminents are reduced, and recycling the hydrotreated solvent to the polymerization reactor.

3 Claims, No Drawings

HYDROTREATING OF RECYCLED BLOCK COPOLYMER SOLVENT

This is a continuation of application Ser. No. 497,010, filed Aug. 8, 1974, now abandoned.

BACKGROUND OF THE INVENTION

This invention is concerned with an improvement in a process for the production of block copolymers.

The block copolymers considered are synthesized by forming a first polymer block of a monoalkenylarene and thereafter block polymerizing a conjugated diene therewith. The process employs a lithium-based initiator and the polymerization is conducted in solvents more fully discussed hereinafter.

After the formation of the first two polymer blocks a number of options exist, including termination of the polymerization, additional block formation or coupling to obtain linear or branched block copolymer configurations.

It has been found that the rate of reactivity of monoalkenylarene with lithium-based polymerization initiators is substantially lowered in the presence of conjugated dienes or other active unsaturated compounds, such as acetylenes. Consequently, if the solvent employed in the block polymerization contains any of these relatively active species, these not only will consume part of the extremely small amount of lithium-based initiator which is present in the system, but also will cause a "skewing", by which is meant the irregular or erratic initiation of polymerization of the monoalkenylarene. This results in the production of a first polymer block having an undesirably broad molecular weight spectrum. Furthermore, due to consumption of an indeterminate amount of the lithium-based initiator, the resulting arene polymer block will have an undesirably high average molecular weight which may vary from batch to batch. These trace impurities also may cause other problems, including gel production and undesirable polymer microstructure.

OBJECTS OF THE INVENTION

It is an object of the present invention to provide an improved process for the preparation of block copolymers. It is a second object of the invention to provide improved process control over the molecular weight of the polymerized product. It is a further object of the invention to provide an efficient and effective method for purification of solvents utilized in the cyclic block copolymer process further described hereinafter. Other objectives will become apparent during the following detailed description of the invention.

STATEMENT OF THE INVENTION

Now, in accordance with the present invention, an improved process is provided for the preparation of block copolymers wherein a first block is formed, utilizing a lithium based polymerization initiator; thereafter block polymerizing a conjugated diene therewith with optional additional block polymerization or coupling stages, after which the block copolymer is separated from the solvent which is recycled to the polymerizer. The recovered solvent is contaminated with up to about 10,000 ppm (parts by weight per million of solvent) of impurites highly reactive with the lithium initiator such as acetylenes, conjugated dienes, halogenated hydrocarbons, esters, coupling agent residues, and mixtures thereof.

The improvement, according to the invention, comprises hydrotreating the contaminated solvent prior to recycle, the hydrotreating preferably being conducted at the solvent recovery temperatures of between about 175°–250° F, utilizing a heterogeneous hydrogenation catalyst having sufficient hydrogenation activity under the conditions employed to permit the weight hourly space velocity of the solvent over the catalyst and in the presence of hydrogen to be greater than about 0.25, the pressure in the system being sufficient to maintain the solvent in an essentially liquid state. Under these conditions the impurities are reduced to innocuous species so that no more than about 10 ppm of the orginal impurites remain in the solvent, which is then recycled to the polymerizer.

The monoalkenylarenes utilized in the formation of at least one of the blocks are preferably monoalkenyl arenes such as styrene, alpha methyl styrene, or tertiary butylstyrene as well as mixtures thereof. The conjugated dienes block-polymerized therewith usually have between four and eight carbon atoms per molecule and include especially butadiene and isoprene as well as mixtures of the same.

The lithium based initiators useful in block copolymer formation may be monofunctional or polyfunctional, lithium alkyls being preferred, including especially those in which the alkyl radical has from 3–8 carbon atoms and molecules. Suitable species include isopropyl lithium, and, preferably, secondary butyl lithium.

The solvents employed in the process are usually capable of essentially completely dissolving both the monomers and the block copolymers made therefrom under the conditions of polymerization at all stages of the polymerization. Hydrocarbon solvents are preferred including alkanes, alkenes, cycloalkanes and cycloalkenes. Preferably the solvent has from 4–8 carbon atoms per molecule. Suitable species and mixtures thereof include isopentane, cyclopentane, hexanes and cyclohexane.

The present process is found to be of special benefit when a single solvent such as cyclohexane (rather than mixtures) is utilized. Conditions may exist where polar modifiers such as ethers or amines may be employed to regulate the microstructure of the polymer block of the conjugated diene as it is being formed.

If the polymerization solvent comprises mixtures of species, these may be hydrotreated as is or fractionated, if desired, and the fractions may be separately treated to remove impurities and later recombined for recycling. The separation of each fraction will depend upon the impurities contained in them. For example, a mixture of isopentanes and cyclohexane may be fractionated initially by distillation. The isopentane fraction may be further separated by taking an overhead of light species including butadiene, the isopentane cut may then be treated to remove any undesirable residuals of butadiene either by hydrotreating or distillation. The cyclohexane, containing trace amounts of contaminants may then be subjected to hydrotreating as described herein.

As referred to hereinabove, the two first essential steps of the polymerization comprise the formation of a first polymer block followed by injection of a second monomer for the purpose of synthesizing the second polymer block. Then, following either termination, further block formation or coupling reactions, the block copolymer is recovered such as by flashing the solvent therefrom. The latter is then recycled (after hydrotreating) to the polymerizer for the formation of additional amounts of block copolymer.

The solvent gradually becomes contaminated with undesirable species in trace amounts, some of which may originate either in the original solvent feed, or are synthesized inadvertently under the temperature and other influences to which they are subjected; or, in the case of dienes, are small residual amounts of diene remaining from the diene monomer addition which did not become polymerized. As stated previously, many of these contaminents are undesirable in their effects upon the initiation of polymerization of monoalkenylarenes conducted in solvent which has been recycled to the polymerizer.

Heretofore other means of purification have been employed. These have included fractional distallation to remove both volatiles and heavy ends and also have comprised the so-called "titration" of the contaminents with lithium based initiator. While the latter is effective for this purpose, it entails the consumption of relatively expensive initiators as well as the buildup of reaction products which may undesirably affect subsequent operations in which the solvent is employed. The present process minimizes or eliminates the requirement for distillation as well as minimizes our eliminating any need for reaction of impurities with lithium based catalysts.

Following polymerization, the block copolymer is recovered from its solvent by flashing operations in which the solvent is flashed off and the polymer is recovered as a "crumb" or a particle which may be as fine as a powder.

The most efficient conduct of the process of this invention comprises utilization of the heat in the flashed or recovered solvent during hydrotreating. For example, the recovery operation usually results in separated solvent which is usually at an elevated temperature between about 150° and 300° F; preferably about 175° and 250° F. In accordance with this preferred aspect of the invention, it has been found that hydrotreatment of the recovered solvent within the recovery temperature range of 150°–300° F is possible, utilizing a highly active hydrogenation heterogeneous catalyst; the solvent being passed over the catalyst under these conditions and, in the presence of an excess of hydrogen, at a weight hourly space velocity (WHSV) greater than 0.25, (preferably greater than 2.0) and at a pressure sufficient to maintain the solvent in an essentially liquid state. WHSV is defined as being the weight of solvent per unit weight of catalyst contacted per hour. Under these conditions, the impurites, such as residual amount of diene, acetylenes, and even of coupling agents or their residues such as halogenated hydrocarbons are reduced and converted to species which are essentially inert toward lithium-based initiators. Normally the total amount of impurities present prior to hydrotreating is in the order of up to 10,000 parts by weight per million parts by weight of the solvent (ppm). After treatment according to the invention it has been found that the solvent contains no more than about 10 ppm of undesired impurities.

The hydrogenation catalysts employed must be selected to meet a number of criteria: First, they must be highly active for the reduction of the contaminants within the above recited temperature range so as to utilize the recovered solvent without any appreciable amount of heat exchanging equipment being required for the feed to the hydrotreater in accordance with the preferred operation of the invention. Secondly, the catalyst should be of the heterogeneous type so that the only step following hydrotreating prior to recycle would at most be simple filtration for the removal of catalyst fines. Third, the catalyst must be active enough under these conditions that satisfactory reduction of contaminants occurs under relatively high WHSV, e.g., greater than 0.25 and usually greater than 2.0. Preferably the catalyst is also capable of virtually complete hydrogenation of contaminants at relatively low pressure, e.g., below about 500 psig so that high pressure equipment and hydrogen compressors are not required. Suitable catalysts include particularly nickel, or nickel/molybdenum deposited on surfaces such as silica, kieselguhr, alumina and the like. Typical of these is Harshaw, NIckel 1404 T, which is nickel deposited on pellets of kieselguhr.

Other suitable commercially available hydrogenation catalysts are HARSHAW Ni 1202 T; GIRDLER GR 65; SHELL Nickel Moly 324.

The following working examples illustrate the process of the present invention.

EXAMPLE I

A block copolymer having the structure polystyrene-polybutadienepolystyrene is prepared in a polymerizer using cyclohexane as solvent. The copolymer is separated from the solvent by flashing under high shear conditions and the solvent is recovered by condensation of the flashed vapors. The recovered solvent is found to be contaminated with about 500 ppm hydrogenatable species, not identified. The content of hydrogenatable species varied and can be determined by ozone titration.

Two samples of recovered cyclohexane are subjected to hydrotreating under the conditions given in Table I, below. The feed to the hydrotreater is mixed with hydrogen in an inert bed packed with Raschig rings while being heated to the hydrotreating temperature. The preheated feed then contacts the hydrogenation catalyst in a column using upflow conditions to maintain liquid full operation. The hydrotreating catalyst is activated HARSHAW Ni 1404 T, which is 70% nickel deposited on kieselguhr pellets of high crush strength. The ozone titration data given in Table I show that essentially complete reduction of hydrogenatable species is achieved. The hydrotreated products are therefore in satisfactory condition for recycle to the polymerizer.

TABLE I

| Run: | 1 | 2 |
|---|---|---|
| Hydrotreater Conditions | | |
| Temperature, ° F | 190 | 210 |
| H₂ pressure, psig | 70 | 50 |
| WHSV | 6.0 | 3.0 |
| Excess H₂ flow, l./min. | 0.25 | 0.25 |
| Ozone Titration | | |
| Feed, meq/g. | 0.0461 | 0.0142 |
| Product, meq/g. | 0.0001 | 0.0001 |

What is claimed is:

1. In the process for preparation of a block copolymer wherein a first monomer of the group consisting of monoalkenyl arenes and conjugated dienes is polymerized in a polymerizer in an inert saturated hydrocarbon solution whereby a first polymer block is formed with a lithium based initiator and thereafter a second monomer of said group is block polymerized therewith after which the block copolymer is separated from the solvent, the separated solvent having a temperature between about 150° and 300° F and being contaminated with up to 10,000 parts per million of impurities reactive with the lithium initiator selected from the group consisting of acetylenes, conjugated dienes, esters, halogenated hydrocarbons and mixtures thereof, and recycling the recovered solvent to the polymerizer for the synthesis of additional quantities of the block copolymer; the improvement comprising hydrotreating the contaminated solvent at about its separation temperature prior to recyle utilizing a heterogeneous nickel/molybdenum hydrogenation catalyst, a weight hourly space velocity greater than about 0.25 and a pressure sufficient to maintain the solvent in an essentially liquid state, whereby the contaminates are reduced to less than about 10 parts per million.

2. A process according to claim 1 wherein the solvent is at least one cycloalkane having 5–7 carbon atoms per molecule.

3. A process according to claim 1 wherein the solvent comprises cyclohexane.

* * * * *